United States Patent [19]
Yamamura et al.

[11] Patent Number: 5,885,964
[45] Date of Patent: Mar. 23, 1999

[54] KININOGEN AGENT PROMOTING BONE FORMATION AND INHIBITING BONE RESORPTION

[75] Inventors: Junichi Yamamura; Yukihiro Takada, both of Kawagoe; Masaaki Goto, Shimotsuga-gun; Seiichiro Aoe, Sayama, all of Japan

[73] Assignee: Snow Brand Milk Products Co., Ltd., Kokkaido, Japan

[21] Appl. No.: 790,370

[22] Filed: Jan. 28, 1997

[30] Foreign Application Priority Data

Feb. 8, 1996 [JP] Japan ................................ 8-045566

[51] Int. Cl.⁶ ............................................... A61K 38/00
[52] U.S. Cl. ............................................. 514/12; 514/16
[58] Field of Search ................................. 514/12, 16

[56] References Cited

U.S. PATENT DOCUMENTS

| | | | |
|---|---|---|---|
| 3,970,520 | 7/1976 | Feldman et al. | 195/29 |
| 4,107,334 | 8/1978 | Jolly | 426/7 |
| 5,114,413 | 5/1992 | Mosher et al. | 604/266 |
| 5,149,647 | 9/1992 | Burling | 435/192 |
| 5,464,820 | 11/1995 | Burton et al. | 514/16 |
| 5,472,945 | 12/1995 | Schmaier et al. | 514/12 |
| 5,516,675 | 5/1996 | Uchida et al. | 435/192 |

FOREIGN PATENT DOCUMENTS

| | | | |
|---|---|---|---|
| 0573668 A1 | 12/1993 | European Pat. Off. | |
| 04183371 | 6/1992 | Japan | A23L 1/305 |
| 05292921 | 11/1993 | Japan | A23L 1/325 |
| 07002896 | 1/1995 | Japan | C07K 14/51 |
| 07082172 | 3/1995 | Japan | A61K 38/43 |
| WO93/00105 | 1/1993 | WIPO . | |
| WO93/13676 | 7/1993 | WIPO . | |

OTHER PUBLICATIONS

Gustafson, et al.; Stimulation of bone resorption . . . osteitis; Bone Mineral, 1 (4), pp. 267–277, 1986.

K. Kussendrager, "Lactoferrin and Lactoperoxydase, Bio-Active Milk Proteins" *IFI NR.6*, pp. 17–21 (1993).

S. Rudloff et al., "Calcium Retention from Milk–Based Infant Formulas, Whey–Hydrolysate Formula, and Human Milk in Weanling Rhesus Monkeys" *AJDC* 144:360–363 (1990).

A. Elzanowski et al., "Cystatin Domains in Alpha–2–HS–Glycoprotein and Fetuin" *FEBS Letters* 227(2):167–170 (1988).

O. Ljunngren et al., "Stimulation of Bone Resorption in Cultured Mouse Calvaria by Met–Lys–Bradykinin" *J. Periodontal Res.* 23(1):75–77 (1988)—Abstract.

*Primary Examiner*—Theodore J. Criares
*Attorney, Agent, or Firm*—Testa, Hurwitz & Thibeault LLP

[57] ABSTRACT

The present invention will provide an agent promoting bone formation and inhibiting bone resorption comprising kininogen and degradation product of kininogen as an effective ingredient. Fragment 1·2 is a preferable degradation product of kininogen.

Further, the present invention will provide a drink, food, medicine and feed combined with kininogen and degradation product of kininogen.

8 Claims, No Drawings

KININOGEN AGENT PROMOTING BONE FORMATION AND INHIBITING BONE RESORPTION

FIELD OF THE INVENTION

The present invention relates to an agent promoting bone formation and inhibiting bone resorption comprising kininogen and/or degradation products of kininogen as an effective ingredient.

Further, the present invention relates to a drink, food, medicine or feed combined with kininogen and/or degradation product of kininogen.

BACKGROUND OF THE INVENTION

Accompanying with the prolongation of human life span, the incidence of metabolic diseases such as osteoporosis, bone fracture, bone pain etc., recently increased. In bone tissue, bone formation and bone resorption are always occurring. While the balance of bone formation and bone resorption is kept in one's youth, bone resorption exceeds bone formation due to various causes as one's age increases (uncoupling). And when bone resorption prolongs for a long duration, bone tissue becomes fragile, which causes metabolic bone diseases such as osteoporosis, bone fracture, bone pain, etc. Therefore, if uncoupling can be inhibited, metabolic bone diseases such as osteoporosis, bone fracture, bone pain, etc. are expected to be prevented.

As conventional methods of preventing or treating metabolic bone diseases by inhibiting uncoupling, (1) calcium supplemented diets, (2) light exercise, (3) sunbathing, (4) medicinal therapy, etc. are exemplified. As for calcium supplemented diets, calcium salts such as calcium carbonate, calcium phosphate, etc., and naturally occurring calcium-containing preparation, such as bovine bone powder, egg shell, fish bone powder, etc. are used. They are, however, not necessarily good for oral intake. As light exercises, jogging or walking may be recommended. However, they are troublesome to a person who becomes weak and quite difficult to an immobilized aged person. Sunbathing is believed to be good for supplement of active form of vitamin $D_3$ but is not sufficient. As medicinal therapy, 1α-hydroxyvitamin $D_3$ and/or calcitonin may be used and they are known to be effective for treating osteoporosis. However, they are medicines themselves and cannot be used as food sources.

On the other hand, the present inventors found that the fraction obtained from whey protein was effective for strengthening bone (Japanese published unexamined patent application No. 183371 (1992)). Further, the present inventors found that the fraction obtained from the above bone strengthening fraction by treating with ethanol, heating, treating with salts or treating with ultrafiltration membrane was effective for stimulating osteoblastic proliferation (Japanese published unexamined patent application No. 176715 (1993) and for strengthening bone (Japanese published unexamined patent application No. 320066 (1993)). In addition, the present inventors found that basic protein fraction present in a very small amount of milk had actions of stimulating osteoblastic proliferation, strengthening bone and inhibiting bone resorption (Japanese patent application No. 207509 (1995)).

The present inventors, further, tried to separate, purify and identify active components of the basic protein having action of stimulating osteoblastic proliferation, strengthening bone and inhibiting bone resorption and eventually found that they were fragment 1·2 of kininogen which was already known. And the inventors also found that kininogen and degradation products of kininogen also had actions of promoting bone formation and inhibiting bone resorption and accomplished the present invention. Accordingly, an object of the present invention is to provide a novel agent promoting bone formation and inhibiting bone resorption comprising kininogen and/or degradation products of kininogen as an effective ingredient. Another object of the present invention is to provide a drink, food, medicine and feed promoting bone formation and inhibiting bone resorption combined with kininogen and/or degradation products of kininogen.

SUMMARY OF THE INVENTION

Accordingly, an object of the present invention is to provide an agent promoting bone formation and inhibiting bone resorption comprising kininogen and/or degradation products of kininogen as an effective ingredient.

Another object of the present invention is to provide a drink, food, medicine or feed combined with kininogen and/or degradation products of kininogen.

DETAILED DESCRIPTION OF THE INVENTION AND PREFERRED EMBODIMENTS

Kininogen used as an effective ingredient in the present invention is known as a precursor of kinin which is a biologically active peptide having action of vasodilation, reducing blood pressure, contraction of uterine smooth muscle and so on. Bovine kininogen was reported to be separated and purified from plasma (Komiya, M., Kato, H. and Suzuki, T., J. Biochem. (Tokyo), vol. 76, p 811, 1974), from milk (Wilson, W. E., Lazarus, L. H. and Tommer, K. B., J. Biol. Chem., vol. 264, p 17777, 1989). The nucleic acid sequence thereof was reported (Kitamura, N., Takagaki, Y., Furuto, S., Tanaka, T., Nawa, H. and Nakanishi, S., Nature, vol. 305, p 545, 1983).

This kininogen can be obtained, for example, by the following steps:

(1) loading bovine plasma on an anion exchange resin to adsorb kininogen-containing fraction;

(2) eluting it with sodium chloride gradient;

(3) loading the eluent on a cation exchange resin to adsorb kininogen-containing fraction;

(4) eluting it with sodium chloride gradient; and (5) purifying it by gel filtration chromatography.

The fragment 1·2 of kininogen used as an effective ingredient in the present invention is a degradation product produced by digestion of bovine high molecular weight kininogen with kallikrein, a protease. The bovine high molecular weight kininogen is glycoprotein comprising a single chain of polypeptide with a molecular weight of about 80 kilo-dalton (by SDS-polyacrylamide electrophoresis) and has a primary structure comprising heavy chain, bradykinin, fragment 1·2 and light chain from amino-terminal thereof. The heavy chain and the light chain thereof are crosslinked by an intramolecular disulfide bond. It is digested by kallikrein to liberate bradykinin and, then, fragment 1·2. Bradykinin is a biologically active peptide having actions of vasodilation, reducing blood pressure, contraction of uterine smooth muscle, etc., is composed of 9 amino acids. Fragment 1·2 is a protein with molecular weight of about 14 kilo-dalton which composes of 110 amino acids comprising many histidines and lysines to form a basic region. The function of fragment 1·2 was not clear yet. Further, in bovine plasma, there is a low molecular weight kininogen which contains bradykinin but does not contain fragment 1·2.

As for this fragment 1·2 of kininogen, for example, it can be obtained by digesting kininogen prepared from bovine plasma by kallikrein digestion and carrying out gel filtration chromatography wherein heavy chain-light chain complex, fragment 1·2 and bradykinin are eluted sequentially (Han, Y. N., Kato, H., Iwanaga, S., Oh-ishi, S. and Katori, M., J. Biochem. (Tokyo), vol. 83, p. 213, 1978).

The degradation product of kininogen used as an effective ingredient in the present invention is a peptide mixture with molecular weight in the range of 100–70,000 which can be obtained by gelfiltration chromatography of kininogen digested with a protease such as kallikrein, plasmin, trypsin, chymotrypsin, pepsin, papain, V8 protease, thermolysin.

The agent promoting bone formation and inhibiting bone resorption of the present invention comprises kininogen, fragment 1·2 of kininogen or other degradation product of kininogen as an effective ingredient. Further, kininogen, fragment 1·2 of kininogen or other degradation product of kininogen can be combined with a drink or food such as milk, milky drink, coffee drink, juice, jelly, cracker, bread, noodle, sausage, etc. and with a medicine in a form of tablet or powder. The action of promoting bone formation thereof can be, further augmented by using it jointly with good absorptive calcium preparation such as calcium chloride, calcium carbonate, calcium lactate, egg shell, milk-derived calcium, etc.

The agent promoting bone formation and inhibiting bone resorption of the present invention can be taken as 100 ng–10 mg per day, several times, separately in an adult. By taking the agent promoting bone formation and inhibiting bone resorption of the present invention, metabolic bone disease such as osteoporosis can be prevented or improved. Acute toxicity of kininogen, fragment 1·2 of kininogen or other degradation product of kininogen was not recognized in rats.

The agent promoting bone formation and inhibiting bone resorption of the present invention comprising kininogen and/or degradation product of kininogen is useful for prevention or improvement of metabolic bone diseases such as osteoporosis etc. In addition, a drink, food, medicine and/or feed combined with these effective ingredients can promote bone formation and/or inhibit bone resorption, which results in prevention or improvement of metabolic bone diseases such as osteoporosis etc.

The present invention will be described by examples as below but these examples will not limit the scope of the present invention.

EXAMPLE 1

According to a known method (Shimada, T., Sugo, T., Kato, H. and Iwanaga, S., J. Biochem. (Tokyo), vol. 92, p 679, 1982), bovine plasma kininogen was prepared. That is, 10 l of bovine plasma was loaded on a DEAE-Sephadex A-50 column (200×100 mm) equilibrated with 20 mM Tris-HCl buffer solution (pH 8.0) containing 50 mM sodium chloride, followed by eluting the adsorbed protein with sodium chloride gradient up to 600 mM. Kininogen was eluted at about 300 mM sodium chloride. Then, this was desalted by dialysis and loaded on a CM-sephadex C-50 column (80×200 mm) equilibrated with 50 mM acetate buffer solution (pH 6.3) containing 0.2M sodium chloride, followed by eluting the adsorbed protein with sodium chloride gradient up to 0.8M. Kininogen was eluted at 0.6M sodium chloride. This was desalted by dialysis and loaded on a Sephadex G-150 column (40×1,000 mm) equilibrated with Tris-HCl buffer solution (pH 8.0) containing 1.0M sodium chloride and 3 mM EDTA, followed by elution to give kininogen, which was desalted by dialysis and lyophilized to give 15.2 mg of high molecular weight kininogen.

EXAMPLE 2

According to a known method (Han, Y. N., Kato, H., Iwanaga, S. and Suzuki, T., J. Biochem. (Tokyo), vol. 79, p 1201, 1976), degradation product of kininogen was prepared by protease treatment of high molecular weight kininogen obtained in example 1. That is, 5 mg of high molecular weight kininogen was dissolved in 2.5 ml of 0.2M ammonium bicarbonate (pH 8.0) and 5 μg of kallikrein derived from bovine plasma was added thereto, which was kept at 37° C. for 1 hour, followed by heating it at 80° C. for 10 minutes to finish the enzymatic reaction. The reaction product was desalted by dialysis and lyophilized to give 4 mg of degradation product of kininogen.

EXAMPLE 3

The degradation product (2.0 mg) of kininogen obtained in Example 2 was loaded on a Sephadex G-75 column (40×1,000 mm) equilibrated with 0.2M ammonium bicarbonate (pH 8.0) and fractionated using a fraction collector. Protein was measured by absorbance at 280 nm. Since a higher molecular weight protein was known to be eluted faster according to a reference (Han, Y. N., et. al., J. Biochem. (Tokyo), vol. 79, p 1201, 1976), the second peak of 3 peaks was collected, desalted by dialysis and lyophilized to give 0.2 mg of fragment 1·2 of kininogen.

EXAMPLE 4

According to a known method (Wilson, W. E., Lazarus, L. H. and Tommer, K. B., J. Biol. Chem., vol. 264, p 17777, 1989), kininogen was prepared from milk. That is, 100 l of milk was centrifuged (5,000×g, 20 min.) to make skim milk, to which hydrochloric acid was added to adjust to pH 4.6. The resulting precipitate was removed by centrifugation (5,000×g, 20 min.). Then, this supernatant was adjusted to pH 6.4 and loaded on a DEAE-Sephadex A-50 column (200×100 mm) equilibrated with 10 mM phosphate buffer solution (pH 6.4) containing 10% methanol, followed by eluting the adsorbed protein with sodium chloride gradient up to 1,000 mM. Kininogen was eluted at about 400 mM sodium chloride. Then, this was desalted by dialysis and loaded on a CM-Sephadex C-50 column (80×200 mm) equilibrated with 10 mM ammonium acetate (pH 4.0) containing 10% acetonitrile, followed by eluting the adsorbed protein with guadinine hydrochloride gradient up to 0.4M. Kininogen was eluted at about 0.2M guanidine hydrochloride. Then, this was desalted by dialysis and loaded on a Sephadex G-150 column (40×1,000 mm) equilibrated with Tris-HCl buffer (pH 8.0) solution containing 1.0M sodium chloride and 3 mM EDTA, followed by eluting kininogen, which was desalted by dialysis and lyophilized to give 1·2 mg of milk-derived kininogen.

EXAMPLE 5

According to a known method (Han, Y. N., Kato, H., Iwanaga, S. and Suzuki, T., J. Biochem. (Tokyo), vol. 79, p 1201, 1976), degradation product of kininogen was prepared by protease treatment of milk-derived kininogen obtained in Example 4. That is, 0.5 mg of milk-derived kininogen was dissolved in 2.5 ml of 0.2M ammonium bicarbonate (pH 8.0)

and 0.5 μg of kallikrein derived from porcine plasma was added thereto, which was kept at 37° C. for 1 hour, followed by heating it at 80° C. for 10 minutes to finish the enzymatic reaction. The reaction product was desalted by dialysis and lyophilized to give 0.4 mg of degradation product of kininogen.

EXAMPLE 6

The degradation product (0.2 mg) of kininogen obtained in Example 5 was loaded on a Sephadex G-75 column (40×1,000 mm) equilibrated with 0.2M ammonium bicarbonate (pH 8.0) and fractionated using a fraction collector. Protein was measured by absorbance at 280 nm. Since a higher molecular weight protein was known to be eluted faster according to a reference (Han, Y. N., et. al., J. Biochem. (Tokyo), vol. 79, p 1201, 1976), the second peak of 3 peaks was collected, desalted by dialysis and lyophilized to give 0.02 mg of fragment 1·2 of kininogen.

TEST EXAMPLE 1

Substances obtained in Example 1–6 were investigated with respect to action of stimulating osteoblastic proliferation. That is, $2\times10^4$ cells/ml of mouse osteoblastic cell line MC3T3-E1 in α-modified minimum essential medium (α-MEM) containing 10% bovine fetal serum (Flow Laboratories) was inoculated in each well of 96-well plate and cultured at 37° C. for 24 hours in the presence of 5% $CO_2$, which was used as cell for test culture. Then, the medium was changed into α-MEM which did not contain bovine fetal serum, to which fraction obtained in Example 1–6 was added to give the final concentration of 10 μg/ml and cultured at 37° C. for 18 hours. Then, 2 hours after 0.02 MBq of $^3$H-thymidine was added thereto, cells were collected on a glass filter by a cell harvester, and radioactivity incorporated into cells was counted by a liquid scintillation counter for determination of proliferative activity of osteoblast. As controls, culture without any addition and one with EGF (epidermal growth factor) addition were used. The proliferative activity in each case was calculated (%) by defining 100% as that in the case of culture without any addition and the results were represented in Table 1.

TABLE 1

|  | Proliferative activity of osteoblast |
| --- | --- |
| Example 1 | 250 ± 23 (%) |
| Example 2 | 234 ± 15 |
| Example 3 | 350 ± 34 |
| Example 4 | 280 ± 28 |
| Example 5 | 260 ± 36 |
| Example 6 | 369 ± 44 |
| EGF | 253 ± 33 |

Comparing with proliferative activity of the non-added group, that of any group with addition of substance obtained in Example 1–6 was higher and or equal to that of the group with EGF addition. Similar results were obtained in the case of test culture using another osteoblastic cell line UMR.

TEST EXAMPLE 2

Substances obtained in Example 1–6 were investigated with respect to inhibiting action on bone resorption. Long bones were obtained from 10–20 days-old ICR mice and the whole bone marrow cells containing osteoclast were obtained by removing soft tissue from the bones and mincing the bones mechanically in α-MEM containing 5% bovine fetal serum. About $2\times10^6$ of these cells in α-MEM containing 5% bovine fetal serum were placed on a piece of dentine. Two hours later, a test sample in α-MEM containing 5% bovine fetal serum was added to give the final concentration of 10 μg/ml, which was cultured for 5 days and bone resorptive activity of osteoclast was investigated.

Analysis of bone resorption was carried out by removing cells from a piece of dentine after cultivation, staining them with Hematoxylin dye and counting the number of bone resorptive pits by morphometrical analysis with PIAS-LA-555. As controls, culture without any addition and one with addition of EGF were used and bone resorptive activity of each case was calculated by defining 100% as that in the case of non-added group. The results are represented in Table 2.

Comparing with bone resorptive activity of non-added group, that of any group with addition of substance obtained in Example 1–6 was prohibited more. It was found that they had an action of inhibiting bone resorption.

TABLE 2

|  | Bone resorptive activity |
| --- | --- |
| Example 1 | 80.6 ± 5.7 |
| Example 2 | 77.7 ± 9.9 |
| Example 3 | 50.4 ± 5.5 |
| Example 4 | 77.6 ± 9.3 |
| Example 5 | 66.5 ± 8.5 |
| Example 6 | 44.4 ± 7.7 |
| EGF | 103.0 ± 4.5 |

EXAMPLE 7

A drink having actions of promoting bone formation and inhibiting bone resorption was prepared by mixing raw materials represented in Table 3, packing it in a container and sterilizing it by heating.

TABLE 3

| Mixed isomerized saccharide | 15.0 (weight %) |
| --- | --- |
| Fruit juice | 10.0 |
| Citric acid | 0.5 |
| Substance obtained in Example 1 | 0.0005 |
| Flavor | 0.1 |
| Calcium | 0.5 |
| Water | 73.9 |

EXAMPLE 8

A tablet having action of promoting bone formation and inhibiting bone resorption was prepared by mixing raw materials represented in Table 4 and formulating it under pressure.

TABLE 4

| Crystalline glucose hydrate | 93.5 (weight %) |
| --- | --- |
| Substance obtained in Example 2 | 0.005 |
| Calcium | 5.0 |
| Sugar ester | 1.0 |
| Flavor | 0.5 |

EXAMPLE 9

A cracker having action of promoting bone formation and inhibiting bone resorption was prepared by mixing raw materials represented in Table 5, making dough, formulating and baking it.

TABLE 5

| | |
|---|---|
| Wheat powder | 50.0 (weight %) |
| Sugar | 20.0 |
| Sodium chloride | 0.5 |
| Margarine | 12.5 |
| Egg | 12.1 |
| Water | 3.7 |
| Sodium bicarbonate | 0.1 |
| Ammonium bicarbonate | 0.2 |
| Calcium carbonate | 0.5 |
| Substance obtained in Example 1 | 0.005 |

EXAMPLE 10

A jelly having action of promoting bone formation and inhibiting bone resorption was prepared by mixing raw materials represented in Table 6, packing it in a container and sterilizing it by heating.

TABLE 6

| | |
|---|---|
| Fructose | 20.0 (weight %) |
| Granulated sugar | 15.0 |
| Millet jelly | 5.0 |
| Agar | 1.0 |
| Substance obtained in Example 4 | 0.0005 |
| Flavor | 0.11 |
| Calcium | 0.1 |
| Water | 58.39 |

EXAMPLE 11

A processed cheese having action of promoting bone formation and inhibiting bone resorption was prepared by mixing raw materials represented in Table 7 and homogenating it at 85° C.

TABLE 7

| | |
|---|---|
| Gouda cheese | 43.0 (weight %) |
| Cheddar cheese | 43.5 |
| Sodium citrate | 2.0 |
| Substance obtained in Example 4 | 0.005 |
| Milk-derived calcium | 1.0 |
| Water | 10.5 |

EXAMPLE 12

After sterilizing 12 weight % reducing defatted milk at 90° C. for 20 min., *Lactobacillus acidophilus* and *Streptococcus thermophilus* were inoculated thereon to give 2 kinds of starter culture, which were mixed in the same amount. A yogurt having action of promoting bone formation and inhibiting bone resorption was prepared by mixing raw materials represented in Table 8 and fermenting it.

TABLE 8

| | |
|---|---|
| Yogurt mix | 97.0 (weight %) |
| Starter culture | 3.0 |
| Substance obtained in Example 4 | 0.0005 |

EXAMPLE 13

A dry milk for infant having action of promoting bone formation and inhibiting bone resorption was prepared by mixing raw materials represented in Table 9.

TABLE 9

| | |
|---|---|
| Skim milk | 75.61 (weight %) |
| Whey protein concentrate | 2.36 |
| Lactose | 13.86 |
| Mineral mixture | 0.32 |
| Water soluble vitamin mixture | 0.32 |
| Fat containing fat-soluble vitamins | 7.53 |
| Substance obtained in Example 4 | 0.001 |

EXAMPLE 14

A feed for dog having action of promoting bone formation and inhibiting bone resorption was prepared by mixing raw materials represented in Table 10.

TABLE 10

| | |
|---|---|
| Soy bean cake | 12.0 (weight %) |
| Skim milk powder | 14.0 |
| Soy bean oil | 4.0 |
| Corn oil | 2.0 |
| Palm oil | 28.0 |
| Corn starch | 15.0 |
| Wheat powder | 9.0 |
| Wheat bran | 2.0 |
| Vitamin mixture | 9.0 |
| Mineral mixture | 2.0 |
| Cellulose | 3.0 |
| Substance obtained in Example 1 | 0.001 |

Combination of these effective ingredients with a drink, food, medicine and feed produces effects on prevention and/or improvement of metabolic bone diseases such as osteoporosis etc. by promoting bone formation and inhibiting bone resorption.

We claim:

1. A method of treating osteoporosis comprising the step of administering to a patient in need of treatment an effective amount of an agent comprising a kininogen or a kininogen peptide.

2. The method according to claim 1, wherein said kininogen peptide is fragment 1·2 of kininogen.

3. A method for promoting bone formation or for inhibiting bone resorption in a mammal comprising administering an amount of kininogen or a kininogen peptide effective for promoting bone formation or inhibiting bone resorption.

4. The method of claim 3, wherein said kininogen peptide is a peptide mixture having a molecular weight of from about 100 to about 70,000 wherein said peptide mixture is obtained by gel filtration chromatography of a product resulting from digestion of kininogen with a protease selected from the group consisting of kallikrein, plasmin, trypsin, chymotrypsin, pepsin, papain, V8 protease and thermolysin.

5. The method of claim 3, wherein said kininogen peptide is fragment 1·2 of kininogen.

6. The method of claim 3, wherein said kininogen or kininogen peptide is administered in a vehicle selected from the group consisting of a food, a drink, a medicine and a feed.

7. The method of claim 1, wherein said kininogen peptide is a peptide mixture having a molecular weight of from about 100 to about 70,000, wherein said peptide mixture is obtained by gel filtration chromatography of a product resulting from digestion of kininogen with a protease selected from the group consisting of kallikrein, plasmin, trypsin, chymotrypsin, pepsin, papain, V8 protease, and thermolysin.

8. The method of claim 1, wherein said kininogen or kininogen peptide is administered in a vehicle selected from the group consisting of a food, a drink, a medicine and a feed.

* * * * *